United States Patent [19]

Goegebeur

[11] Patent Number: 5,449,841

[45] Date of Patent: Sep. 12, 1995

US005449841A

[54] PROCESS FOR PURIFYING POLYOLS

[75] Inventor: Patrick M. G. Goegebeur, Zedelgem, Belgium

[73] Assignee: Imperial Chemical Industries, PLC, London, England

[21] Appl. No.: 321,506

[22] Filed: Oct. 12, 1994

[30] Foreign Application Priority Data

Dec. 13, 1993 [GB] United Kingdom ............... 9325468

[51] Int. Cl.$^6$ .................. C07C 29/76; C07C 29/86; C07C 31/18

[52] U.S. Cl. .................. 568/854; 568/810; 568/621; 568/840; 568/853

[58] Field of Search ............. 568/840, 852, 853, 854, 568/810, 621

[56] References Cited

U.S. PATENT DOCUMENTS

| | | | |
|---|---|---|---|
| 4,038,329 | 7/1977 | Palmer | 568/854 |
| 5,010,047 | 4/1991 | Schuchart | 502/24 |
| 5,099,075 | 3/1992 | Katz et al. | 568/621 |
| 5,144,093 | 9/1992 | Reisch et al. | 568/621 |
| 5,248,833 | 9/1993 | Hinney et al. | 568/621 |

FOREIGN PATENT DOCUMENTS

| | | | |
|---|---|---|---|
| 0576132 | 12/1993 | European Pat. Off. | |
| 1093133 | 5/1986 | Japan | 568/854 |
| 1369304 | 10/1974 | United Kingdom | |

*Primary Examiner*—Werren B. Lone

[57] ABSTRACT

A process for reducing the level of metal ions and/or metal compounds in a polyoxyalkylene monool or polyol having a number average molecular weight of above 500–25000 by bringing the monool or polyol into contact with an extracting compound which is a polyol or a polyol mixture having a number average molecular weight of at most 500 and being immiscible with the polyoxyalkylene monool or polyol, mixing the extracting compound and the polyoxyalkylene monool or polyol, allowing the extracting compound and the polyoxyalkylene monool or polyol to separate and removing the extracting compound.

8 Claims, No Drawings

PROCESS FOR PURIFYING POLYOLS

The invention is concerned with a process for preparing polyoxyalkylene monools or polyols having a reduced amount of metal ions and/or metal compounds.

It is known that in preparing polyoxyalkylene monools or polyols by alkoxylation of an initiator having at least one reactive hydrogen atom, in particular at least one hydroxyl group, catalysts like KOH, NaOH and CsOH may be used.

Surprisingly, it has been found that the level of these catalysts after the preparation of these polyoxyalkylene monools or polyols can be reduced by extraction with certain low molecular weight polyols.

Consequently the invention is concerned with a process for reducing the level of metal ions and/or metal compounds in a polyoxyalkylene monool or polyol having a number average molecular weight of above 500–25000 by bringing the monool or polyol into contact with an extracting compound which is a polyol or a polyol mixture having a number average molecular weight of at most 500, preferably at most 250, and being immiscible with the polyoxyalkylene monool or polyol, mixing the extracting compound and the polyoxyalkylene monool or polyol, allowing the extracting compound and the polyoxyalkylene monool or polyol to separate and removing the extracting compound.

The polyoxyalkylene polyols preferably have a nominal average functionality of 2–8, most preferably of 2–6, and preferably a number average molecular weight of 1000–10000. The polyoxyalkylene monools preferably have a number average molecular weight of 1000–10000.

Such polyoxyalkylene polyols are made by the alkoxylation of an initiator having at least two reactive hydrogen atoms in the presence of an alkoxylation catalyst containing metal, like K, Na, Cs, Ba, Sr; e.g. KOH NaOH and CsOH. In particular K, Na and Cs compounds are often used. The amount of catalyst used generally will range from 100–50000 and preferably from 500–30000 ppm of metal calculated on the amount of polyol made. The same applies to monools with the proviso that the initiator used contains only one reactive hydrogen atom, like e.g. methanol, ethanol, propanol and allyl alcohol and mixtures thereof.

The initiators for preparing the polyols may be selected from those conventionally used like ethylene glycol, diethylene glycol, propylene glycol, dipropylene glycol, butane diol, glycerol, trimethylolpropane, pentaerythritol, sucrose, sorbitol, ethylene diamine, ethanolamine, diethanolamine, triethanolamine, toluene diamine, diphenylmethane diamine and diethyltoluene diamine. Mixtures of initiators may be used as well.

The alkoxylation may be conducted with the alkylene oxides conventionally used like e.g. ethylene oxide, propylene oxide, butylene oxide and mixtures thereof.

The monools or polyols may be homopolymers, random copolymers, block copolymers and random-block copolymers.

The extracting compounds preferably are selected from the group consisting of ethylene glycol, diethylene glycol, triethylene glycol, tetraethylene glycol, glycerol and butanediol and mixtures thereof; ethylene glycol and diethylene glycol and mixtures thereof being most preferred.

Immiscibility in the context of the present invention is defined as follows: an extracting compound is considered as immiscible if at most 30% by weight of the extracting compound can be dissolved in the polyoxyalkylene monool or polyol at room temperature.

The extraction process is carried out as a conventional extraction process. It may be carried out batchwise or continuously. If the process is carried out batchwise this may be done once or more, preferably 1–5 times, most preferably 1 or 2 times.

The extraction process may be conducted at room temperature or at elevated temperature provided the temperature applied is lower than the boiling point of the extracting compound under the conditions applied and than the temperature at which the polyoxyalkylene polyol would disintegrate under the conditions applied. Preferably the temperature will range from 75° to 250° C. Once the monool or polyol and the extracting compound have been combined they are mixed. This may be a normal mixing or a mixing under high shear conditions. The amount of extracting compound used may vary between wide ranges. Preferably the weight ratio of extracting compound and monool or polyol is at least 0.25:1 and more preferably 0.3–5:1.

In case the polyols contain unsaturation, as is usually the case with polyols based on propylene oxide, such unsaturation may be partially removed by the above extraction. The metal in the extracting compound may be recovered if desired.

The invention is illustrated by the following example.

An EO/PO polyol having a molecular weight of 6000, an unsaturation value of 0.068 meg/g (mercuri acetate method), a nominal functionality of 3 and 15% by weight EO (tipped), which was prepared using 0.2% by weight of KOH (the polyol once made contained 1400 ppm of $K^+$), was subjected to extraction by adding diethylene glycol (w/w ratio polyol/glycol=1:1) at room temperature, followed by mixing and heating to 200° C. in about 20 min. Then the mixture was kept at 200° C. for 2 hours and then allowed to stand at room temperature without stirring for 15 hours. The two layers which were formed were separated. The polyol was then subjected to vacuum stripping (200° C., 2 mbar, 8 hours, $N_2$-flow) in order to remove residual diethylene glycol.

The polyol (top-layer) so obtained contained 3 ppm $K^+$ (atomic absorption analysis) and had an unsaturation value of 0.047 meg/g (mercuric acetate method).

I claim:

1. A process for reducing the level of metal ions and/or metal compounds in a polyoxyalkylene monool or polyol having a number average molecular weight of above 500–25000 by bringing the monool or polyol into contact with an extracting compound which is a polyol or a polyol mixture having a number average molecular weight of at most 500 and being immiscible with the polyoxyalkylene monool or polyol, mixing the extracting compound and the polyoxyalkylene monool or polyol, allowing the extracting compound and the polyoxyalkylene monool or polyol to separate and removing the extracting compound.

2. Process according to claim 1 characterised in that the polyoxyalkylene monool or polyol comprises 100–50000 parts per million of metal ions before the extracting compound is added.

3. Process according to claim 1 characterised in that the process is conducted in a continuous way.

4. Process according to claim 1 characterised in that the process is conducted 1 or 2 times batchwise.

5. Process according to claim 1 characterised in that the extracting compound is selected from the group consisting of ethylene glycol, diethylene glycol, triethylene glycol, tetraethylene glycol, glycerol and butanediol and mixtures thereof.

6. Process according to claim 1 characterised in that the extracting compound is selected from the group consisting of ethylene glycol and diethylene glycol and mixtures thereof.

7. Process according to claim 1 characterised in that the polyoxyalkylene monool or polyol before the extracting compound is added comprises Na, K and/or Cs ions and/or compounds.

8. Process according to claim 1 characterised in that the number average molecular weight of the extracting compound is at most 250.

* * * * *

UNITED STATES PATENT AND TRADEMARK OFFICE
CERTIFICATE OF CORRECTION

PATENT NO. : 5,449,841
DATED : SEPTEMBER 12, 1995
INVENTOR(S) : GOEGEBEUR

It is certified that error appears in the above-identified patent and that said Letters Patent is hereby corrected as shown below:

Claim 7, column 4, line 5, "Nag" should read --Na,--.

Signed and Sealed this

Fourteenth Day of May, 1996

Attest:

BRUCE LEHMAN

Attesting Officer   Commissioner of Patents and Trademarks